United States Patent [19]

Weissenburger

[11] Patent Number: 4,946,389

[45] Date of Patent: Aug. 7, 1990

[54] APPLICATOR AND TIPS FOR STAIN REMOVAL

[75] Inventor: Edward A. Weissenburger, Mercerville, N.J.

[73] Assignee: Johnson & Johnson Consumer Products, Inc., New Brunswick, N.J.

[21] Appl. No.: 200,812

[22] Filed: May 31, 1988

[51] Int. Cl.[5] .............................................. A61C 3/06
[52] U.S. Cl. .................................... 433/142; 433/216
[58] Field of Search ............... 433/142, 216, 215, 166, 433/80, 141; 132/321

[56] References Cited

U.S. PATENT DOCUMENTS

| | | | |
|---|---|---|---|
| 656,479 | 8/1900 | Schellenbach | 132/321 |
| 875,824 | 1/1908 | Knisely | 433/142 |
| 1,427,503 | 8/1922 | Wake | 433/166 |
| 4,780,083 | 10/1988 | Croll | 433/132 |

Primary Examiner—John J. Wilson
Attorney, Agent, or Firm—Paul A. Coletti

[57] ABSTRACT

An applicator with attachable tips for tooth stain removal. The applicator can be used manually or in conjunction with the dentist's drill. The tips are generally disposable.

8 Claims, 2 Drawing Sheets

APPLICATOR AND TIPS FOR STAIN REMOVAL

FIELD OF THE INVENTION

The present invention generally relates to an applicator for stain removal. More specifically, the present invention relates to an applicator for the removal of stains on teeth.

BACKGROUND OF THE INVENTION

Frequently teeth can become stained with poor dental care. That is, without proper dental care the teeth will take on a yellowish color. This is due, in large part, to reaction of teeth to such things as nicotine and tar in cigarettes, stains from food, tartar and plaque build-up, and the like. In later stages of discoloration, the teeth will go from a yellowish color to a more black color. These stains can prove unsightly and also hygienically unfavorable. The more stained a tooth becomes, generally the more likely the tooth is to totally decay, necessitating removal from the mouth.

Often, conventional techniques will work for stain removal. That is, a mildly abrasive material will be applied with the dentist's drill. This type of removal will suffice where the teeth are not stained to a more excessive extent. Also, this type of dental hygiene is aided where there is frequent brushing and cleaning with dental floss and the like. This type of cleaning will be most effective if done repeatedly over a six-month period of time. For longer stretches without this type of dental care, the cleaning procedures must necessarily be made more abrasive and can become quite painful to the patient. Unfortunately, in some cases the more conventional techniques are quite useless. That is, the teeth become so stained and blackened that removal of the stain is virtually impossible without resorting to more drastic measures. A system must be created in order for the teeth to be cleaned with highly abrasive material and for long periods of time. This can cause excessive bleeding of the gums and abrasion of the enamel in the teeth. Such abrasive techniques are therefore not necessarily desirable, but have been followed as a type of last resort to combat stain.

On the other hand, many of the present techniques are simply ineffective for cleaning teeth that are excessively stained. Frequently, where there has been no dental care or an extreme lack in the amount of dental care, any of the present techniques will not remove the more permanent stains on the teeth.

SUMMARY OF THE INVENTION

It is an object of the present invention to provide an applicator by which effective stain removal can be made in the worse cases of dental stain. One of the objects of the invention is to be able to clean teeth, either as a group or individually. It is also, of course, desirable to be able to clean between the teeth in the inter-dental spaces.

These and other objects of the present invention are accomplished in an applicator and its attachable tips or collars used for dental stain removal. The applicator will generally be a cylindrical shaft capable of being gripped by the operator. This shaft may also be adapted to fit within a dentist's slow speed handpiece. On the end of the applicator, there is provided a collar which holds a slurry-like material. This slurry is a highly concentrated stain remover. The applicator can be operated to achieve a brushing action across the teeth, either manually or by rotation of the dentist's handpiece. On the other end of the applicator is a pointed tip for removal of stains between the teeth and near the gums. In addition, on the edge of the applicator when connected to the dentist's drill there are a plurality of pockets for buffing the teeth, again using the highly concentrated slurry stain remover.

These and other objects of the present invention can be more readily understood by taking the following description of the drawings in conjunction with the following detailed description of the invention in which:

DETAILED DESCRIPTION OF THE INVENTION

Figure 1:
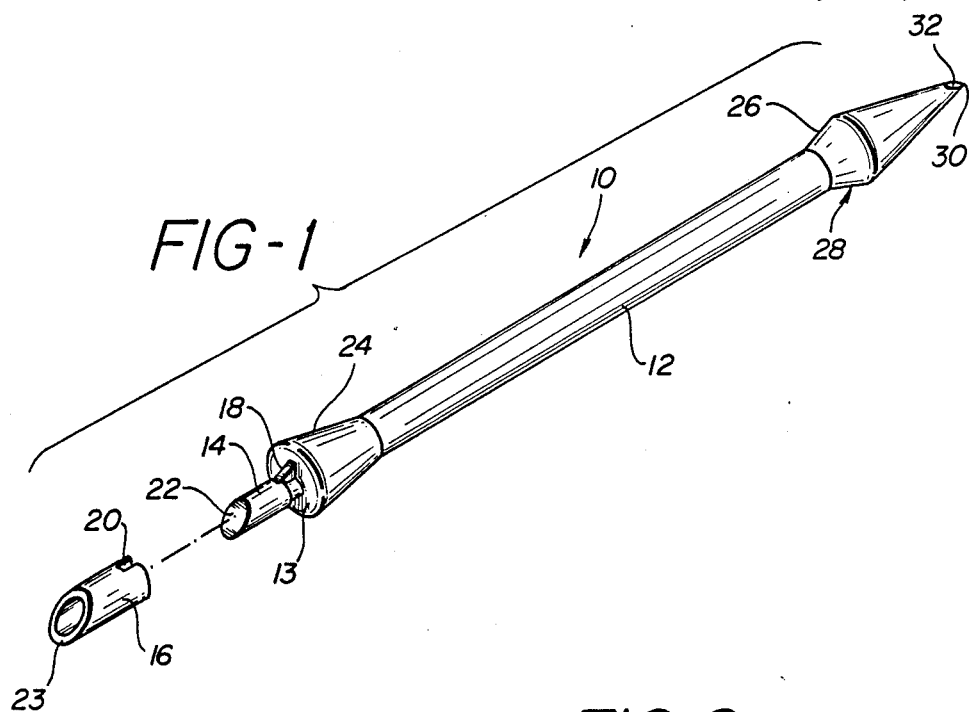
FIG. 1 is a perspective view of a preferred embodiment of the applicator of the present invention.
Figure 2:
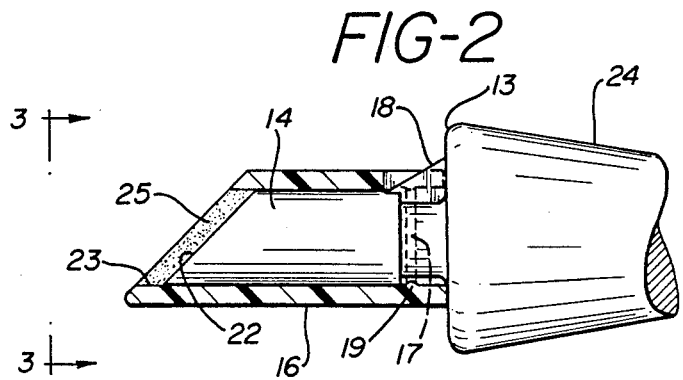
FIG. 2 is an elevational view partially in cross-section of an end of a preferred embodiment of the applicator of the present invention.
Figure 3:
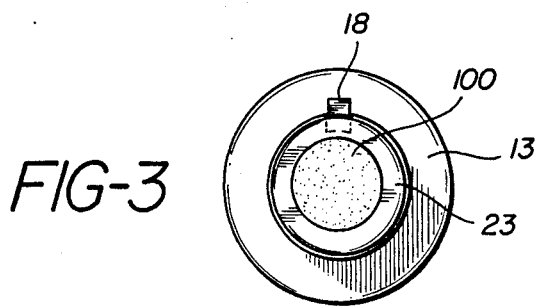
FIG. 3 is an elevational view of one of the ends of an applicator of the present invention as taken along lines 2—2 of FIG. 2.

Turning now to FIGS. 1 through 3, a preferred embodiment of the present invention is shown as the applicator 10. This applicator 10 has a generally cylindrical shaft 12 which has a first shaft end 13. The shaft 12 is configured such that the overall length of the applicator 10 provides good balance to the dentist during use, and easy placement at the work station when not in use. At the end of the first shaft end 13 there is an extension tip or dowel 14. This tip or dowel 14 is connected as an extension to the first end shaft 13. The tip or dowel 14 is a part of the applicator 10 upon which a collar 16 can be attached. The attachment of the collar 16 is better seen in FIGS. 2 and 3.

As seen in FIG. 1, the collar 16 is attached to the tip or dowel 14 so that the key 18 on the dowel 14 aligns with the notch 20 in the collar 16. The key 18 on the dowel 14 provides structural reinforcement to the generally smaller diameter of the dowel 14 from the larger diameter of the cylindrical shaft 12. An internal bead 19 on the collar 16 meshes with a notch 17 on the dowel 14 to lock the collar 16 in place on the dowel 14. These locking mechanisms allow the applicator to be used such that the collar 16 will not rotate around the dowel 14, and such that the hollow 25 created between the dowel 14 and the collar 16 will always be properly aligned for maximum placement of abrasive slurry.

As can be further seen in FIG. 2, the dowel 14 has a wedge shaped end 22. This wedge shaped end 22 falls short of the wedge shaped end 23 of the collar 16. This wedge shaped end 23 is rounded for safety at the gum line. The overlap of the wedge shaped edge 23 with the dowel 14 creates a hollow 25. It is to be noted that the generally flat wedge shaped end 22 can be slightly excavated to form a larger hollow 25. This hollow 25 can be filled with a cleaning solution or slurry 100, as best seen in FIG. 3.

As also can be seen in FIGS. 1 and 2, the applicator has a tapered handle or gripping area 24. This allows the user to more easily manage the motion of the collar 16 containing slurry 100 on the teeth. The angular shape of the gripping area 24 provides good finger support for the dentist, so that hard pressure may be applied to the teeth during the cleaning procedure. The handle 24 also will have rounded corners to ensure safety of the patient's gums during cleaning.

As also seen in FIG. 1, the applicator 10 has a second shaft end 28. This second shaft end 28 is also abutted by a tapered handle or gripping area 26, used for gripping and managing the second shaft end 28 and to apply pressure during cleaning. The second shaft end 28 generally tapers away from the shaft 12, culminating in a point 30. At the end of this point 30 there is a hollow 32. Similar to the hollow 25, this hollow 32 can be rounded to provide a larger volume. In hollow 32 the slurry 100 can be placed.

In this particular embodiment of the present invention, the shaft 12 of the applicator 10 is generally formed from an autoclavable thermoplastic material with a high modulus of elasticity to give it good stiffness in addition to compatibility with the mouth and gums. On the other hand, the material of the collar 16 and point 30 provides elasticity and softness; some pliable plastic, such as Santoprene*, sold by the Monsanto Corporation, can be desirable. It is also desirable to make the collar 16 clear, to ensure visibility of the slurry 100. One other desirable feature is to make the collar 16 disposable, so that it will be replaced for each patient.

In addition, the collar 16 and dowel 14 both have wedge shaped ends 22 and 23 respectively, which preferably have angles of about 45° with the shaft axis. This allows the most easy application of the slurry 100 to the teeth. The slurry 100 will generally be formed from a hydrochloric acid solution or other extremely acidic, strongly abrasive paste. Generally, the hydrochloric acid is combined with distilled water and silicon carbide in order to form a compatible paste which can be applied individually or to groups of teeth and thereby clean each tooth as well as the interproximal areas.

In use, the applicator 10 is applied to the surface of the tooth manually by use of the collar 16 and dowel 14 combination. The dentist is able to rub the tooth with the slurry 100 in order to most efficiently clean the badly stained tooth. When the dentist is satisfied with the results of this more general cleaning process, the dentist can turn the applicator to its other side and use the hollow area 32 at the end of the point 30 in order to clean excessively tough spots or hard-to-get places such as the interproximal areas. In total, about one micron thickness of enamel is removed. This enamel is then reabsorbed by the teeth to give them both a clean appearance and a safe, hygienic surface. After use, the disposable collar 16 is simply thrown away while the remainder of the applicator 10 is autoclaved and then ready for use on another patient.

Figure 4:
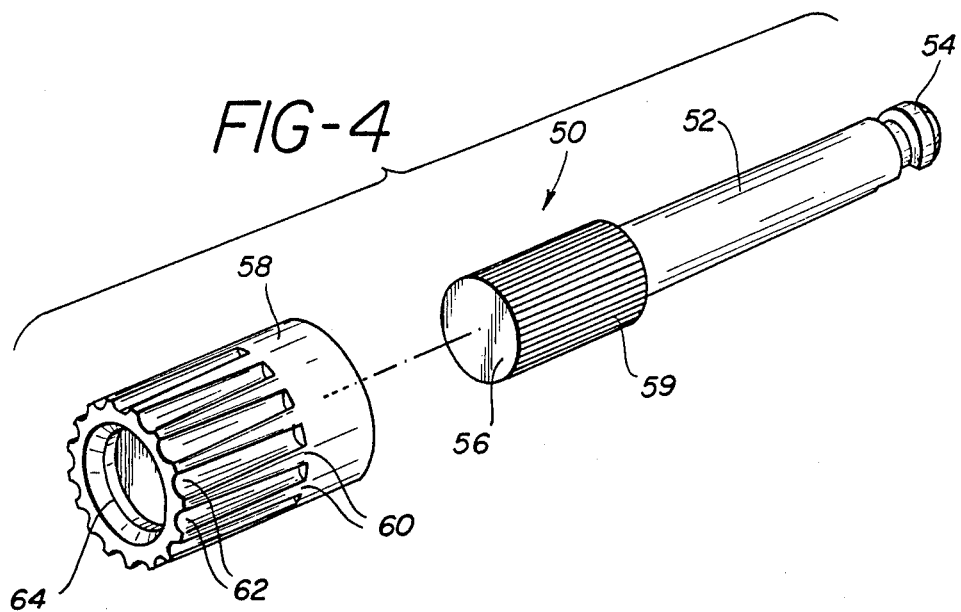
FIG. 4 is a perspective view of the applicator of the present invention as adapted to fit on a dentist's handpiece.
Figure 5:
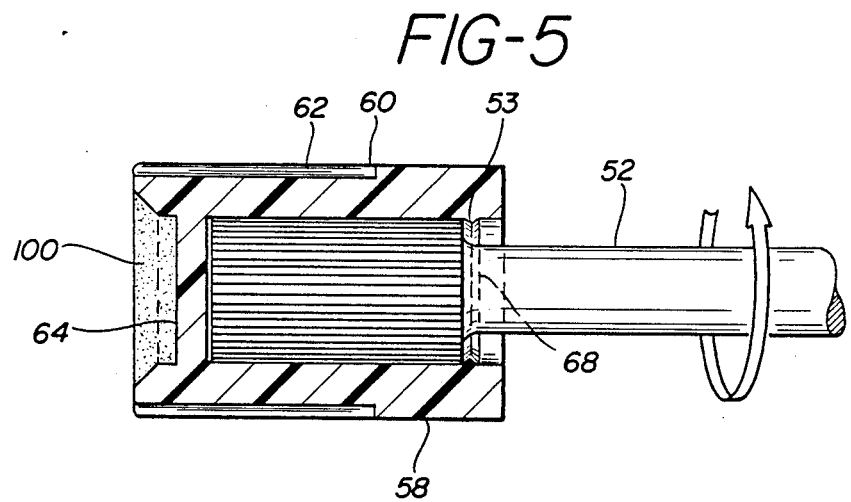
FIG. 5 is an elevational view partially in cross-section of the tip of the applicator of the present invention as seen in FIG. 4.

In addition, this device can be used in conjunction with a dentist's handpiece. As seen in FIGS. 4 and 5, the applicator 52 contains a mandrel 52. Generally, the mandrel 58 is formed from autoclavable stainless steel. This mandrel 52 contains a first mandrel end 54 which is adaptable for emplacement in a typical dentist's handpiece. The second mandrel end 56 is capable of maintaining a collar or cleaning bit 58 in a friction fit. This is accomplished on the knurled surface 59 of the generally cylindrical second mandrel end 56.

This collar 58 is symmetrical for good balance during rotation, and is generally formed from the same disposable thermoplastic as the collar 16 of the original embodiment. It can also be molded from a clear material if visibility is necessary. As seen in FIG. 4, the collar 58 contains ridges 60 which generally can extend the entire length of the collar 58. These ridges 60 form pockets 62. In addition, there is a countersunk pocket 64 as the top of the collar 58. Both the pockets 62 and the countersunk pocket 64 hold slurry 100.

Other features of the collar or cleaning bit 58 are evident in FIG. 5. There is a thickness 66 of material between the end 56 of the mandrel 52 and the counter sunk pocket 64. This provides a soft base for the application of slurry, and prevents premature breakthrough of the mandrel 52. As well there is an internal bead 68 on the collar 58 which meshes with a notch 53 on the mandrel 52, to provide locking of the mandrel 52 with the collar 58. This also allows the collar 58 to extend over the knurled surface 59 of the mandrel 58, in order to further protect the mouth of the patient from contacting the mandrel 52.

In use therefore, the dentist will attach the applicator 50 to the handpiece. The teeth can be buffed along the pockets 62 while the handpiece is spinning, usually at an extremely slow (less than 150 rpm) rate. Individual teeth can be more aggressively attacked by use of the countersunk pocket 64. In addition, of course, the handheld applicator 10 can be used for more particular cleaning.

The present invention has been disclosed in connection with the present preferred embodiment. It will be understood by those skilled in the art that various changed and modifications can be made without departing from the scope of the invention, which is defined by the following claims and their equivalents.

What is claimed is:

1. A device for cleaning teeth comprising:
   a shaft culminating in two ends;
   the first of said shaft ends culminating in a tip, said end adapted for emplacement of a collar;
   a collar fitting over said tip and extending beyond said tip wherein a space is created between the edge of said tip and the edge of said collar;
   the second of said shaft ends culminating in a point, said point surrounding a hollow;
   wherein said hollow of said point and said space created between said tip and the edge of said collar are adapted for emplacement of a tooth cleanser; and
   wherein said collar is generally cylindrical and formed to be placed over said tip in an interference fit, said collar containing a notch on a first end and generally formed to fit against said first shaft end, said first shaft end containing a key extending along said tip to accommodate said notch, said key and notch combination preventing rotation of said collar on said tip.

2. The device of claim 1 wherein said collar and said tip each contain a wedge-shaped end such that when said collar is placed over said tip said collar wedge-shaped end extends beyond said tip wedge-shaped end such that said space created between said collar and said tip is generally wedge-shaped.

3. The device of claim 1 wherein said hollow is generally wedge-shaped.

4. The device of claim 1 wherein said shaft ends each contain outwardly tapered handles for gripping said device.

5. A device for cleaning teeth comprising:
a generally cylindrical shaft culminating in two generally flat ends, said shaft adapted for gripping;
said first generally flat shaft end extended by a generally cylindrical dowel, said cylindrical dowel narrower in diameter than said shaft, said dowel having a generally tapered end, said dowel further adaptable for emplacement of a collar over said dowel; a generally cylindrical collar emplaced over said dowel, said collar abutting said shaft end, and extending beyond said tapered end of said dowel creating a holding space within said collar; and
wherein said collar contains a notch adapted to fit over a key extending from said dowel, such that said key and notch combination preventing rotation of said collar on said dowel.

6. The device of claim 5 wherein said holding space is generally wedge-shaped to conform to the outer edge of said collar extending beyond said dowel.

7. The device of claim 6 wherein said collar further comprises an internal bead and said dowel further comprises a notch such that said internal bead locks said collar on said notch.

8. The device of claim 6 wherein said shaft, said point and said collar are formed from thermoplastic material.

* * * * *